United States Patent [19]

Fischer

[11] Patent Number: 5,554,159

[45] Date of Patent: *Sep. 10, 1996

[54] INSTRUMENT FOR ELECTRO-SURGICAL EXCISOR FOR THE TRANSFORMATION ZONE OF THE UTERINE CERVIX AND METHOD OF USING SAME

[76] Inventor: Nathan R. Fischer, 17 Lovelace Dr., West Hartford, Conn. 06117

[*] Notice: The term of this patent shall not extend beyond the expiration date of Pat. No. 5,403,310.

[21] Appl. No.: 361,747

[22] Filed: Dec. 22, 1994

Related U.S. Application Data

[63] Continuation-in-part of Ser. No. 192,132, Feb. 4, 1994, Pat. No. 5,403,310.

[51] Int. Cl.⁶ .................................................. A61B 17/39
[52] U.S. Cl. ................................................. 606/45; 606/49
[58] Field of Search ................................. 606/32, 33, 37, 606/39–41, 45–47, 49, 119, 170; 128/122, 639, 642, 649

[56] References Cited

U.S. PATENT DOCUMENTS

| | | |
|---|---|---|
| 1,741,740 | 12/1929 | Sederholm et al. . |
| 2,447,169 | 8/1948 | De Sousa . |
| 4,485,812 | 12/1984 | Harada et al. . |
| 4,834,095 | 5/1989 | Miller . |
| 4,846,175 | 7/1989 | Frimberger . |
| 4,887,593 | 12/1989 | Wiley et al. . |
| 4,924,882 | 5/1990 | Donovan . |
| 5,133,713 | 7/1992 | Huang et al. . |

OTHER PUBLICATIONS

Cabot Medical "Cryomedics Disposable Lletz Electrodes" Catalog ZSI–UA. 3/94.Bo.
Ellman International Catalog B11–M–1099 pp. 7, 8, 19 and Back Cover.

*Primary Examiner*—Angela D. Sykes
*Assistant Examiner*—Stephen D. Huane

[57] ABSTRACT

An electro-surgical instrument for excision of a tissue specimen from the transformation zone of the uterine cervix includes an elongated body member with an endocervical portion at one end, a contact portion at the other end, and a vaginal portion therebetween. A stop arm extends at a right angle to the body member at the juncture of the endocervical and vaginal portions, and a wire electrode extends diagonally between the stop arm and endocervical portion. Preferably the stop arm has a laterally offset portion intermediate its length to enable observation of the electrode cutting action over most of its length. In using the instrument, the endocervical portion is inserted through the vaginal canal and into the endocervical canal of the uterine cervix until the electrode contacts an area of the ectocervix without colposcopically evident pathology. Current is imparted to the electrode and the instrument is advanced into the endocervical canal until the stop arm abuts the ectocervix, after which the instrument is rotated one full revolution to cut a conically shaped tissue specimen from the transformation zone of the uterine cervix which is withdrawn with the instrument.

8 Claims, 4 Drawing Sheets

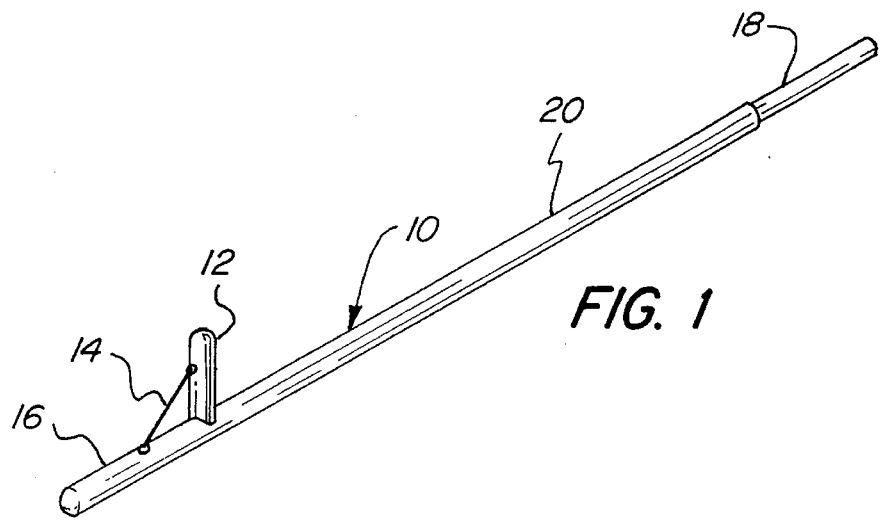
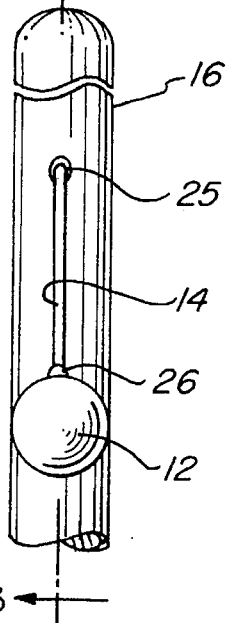
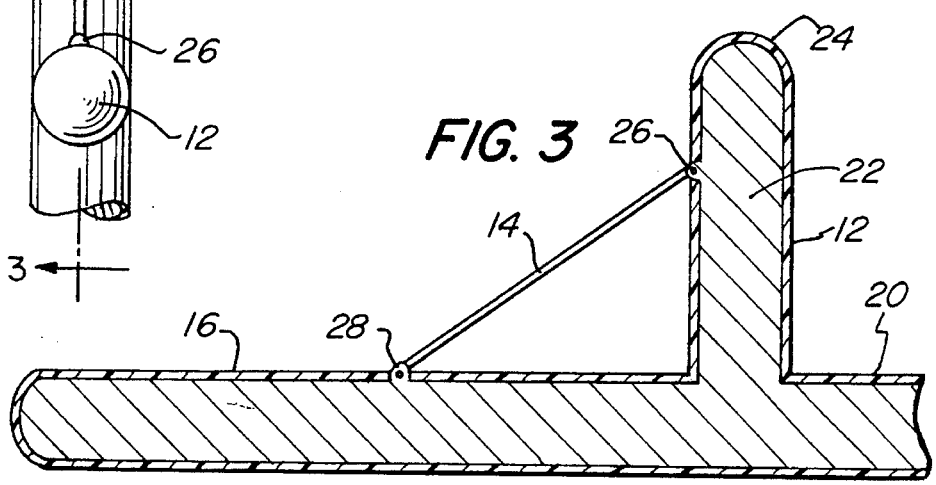

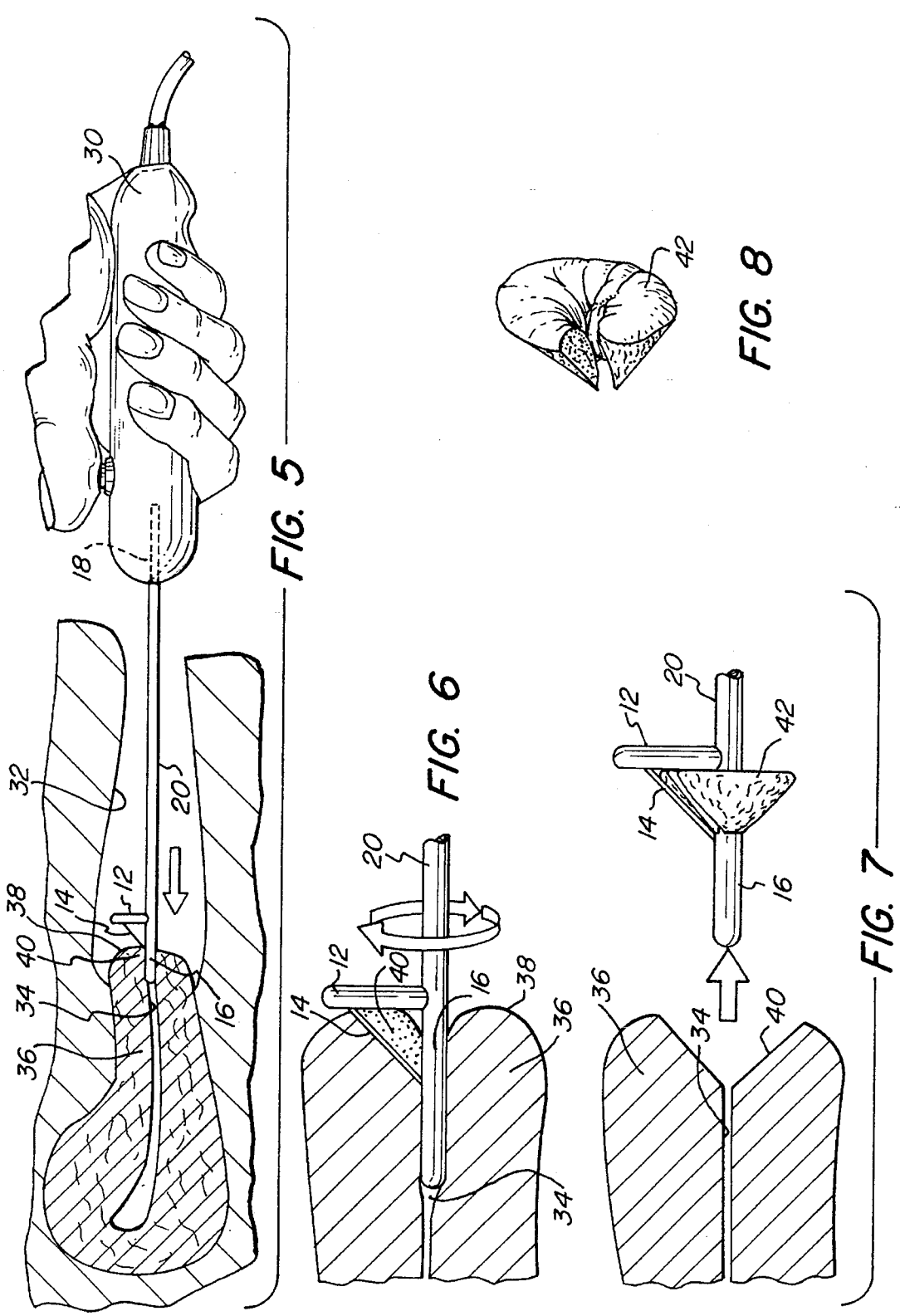

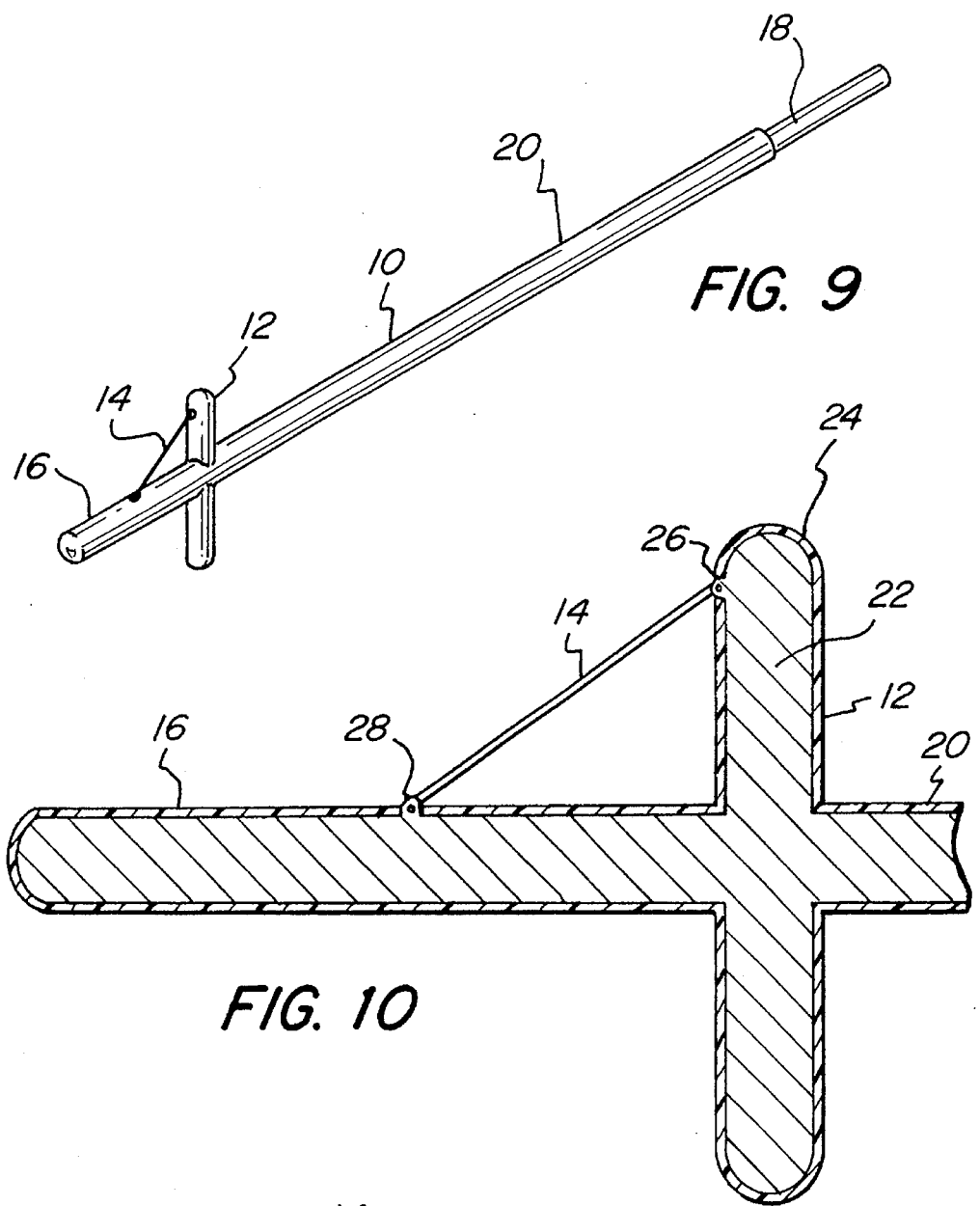
FIG. 9
FIG. 10
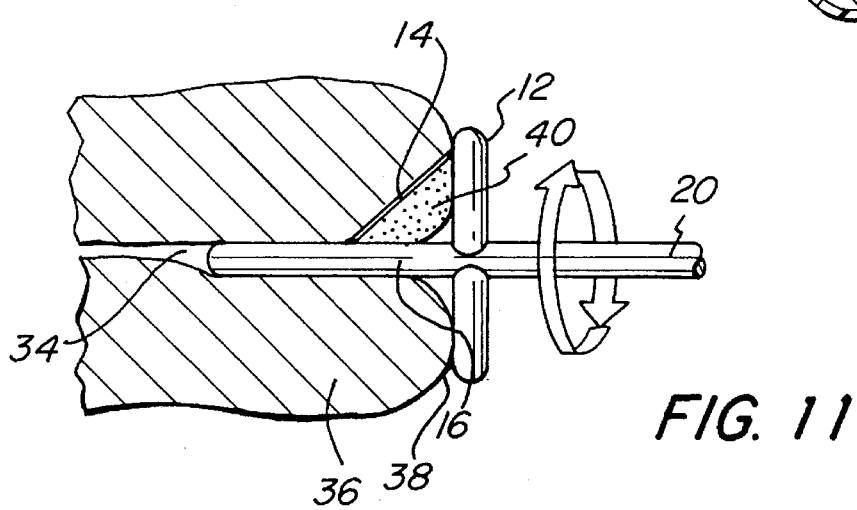
FIG. 11

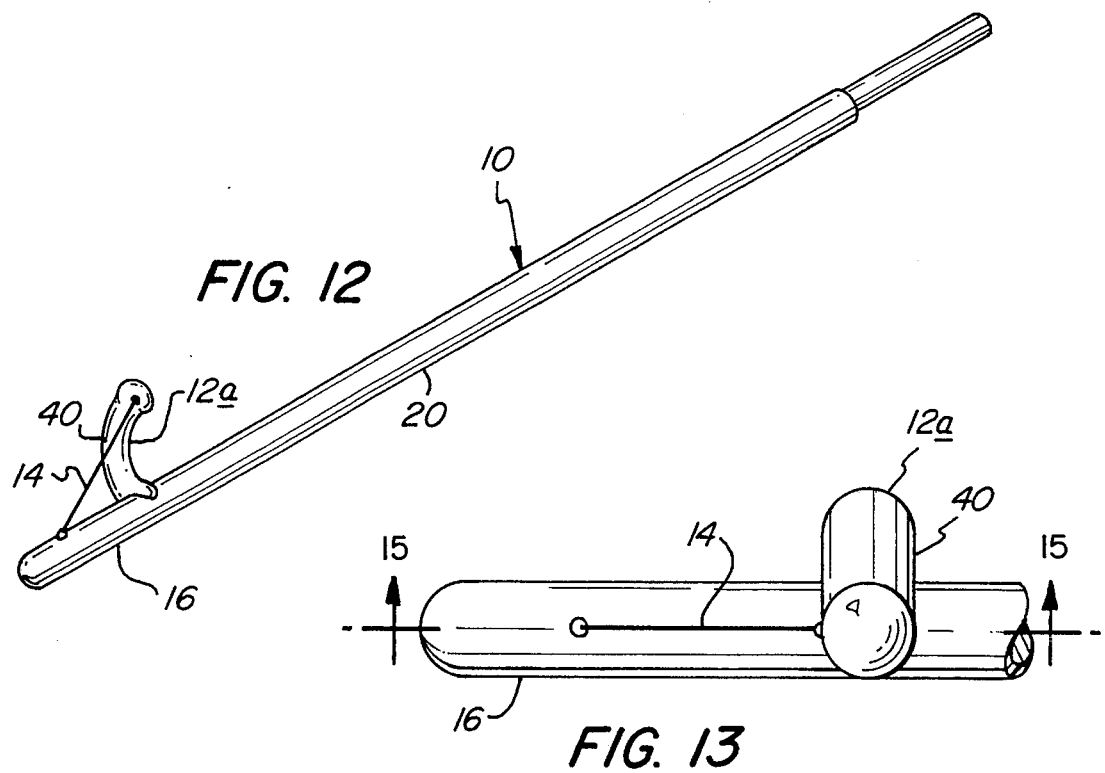
FIG. 12
FIG. 13
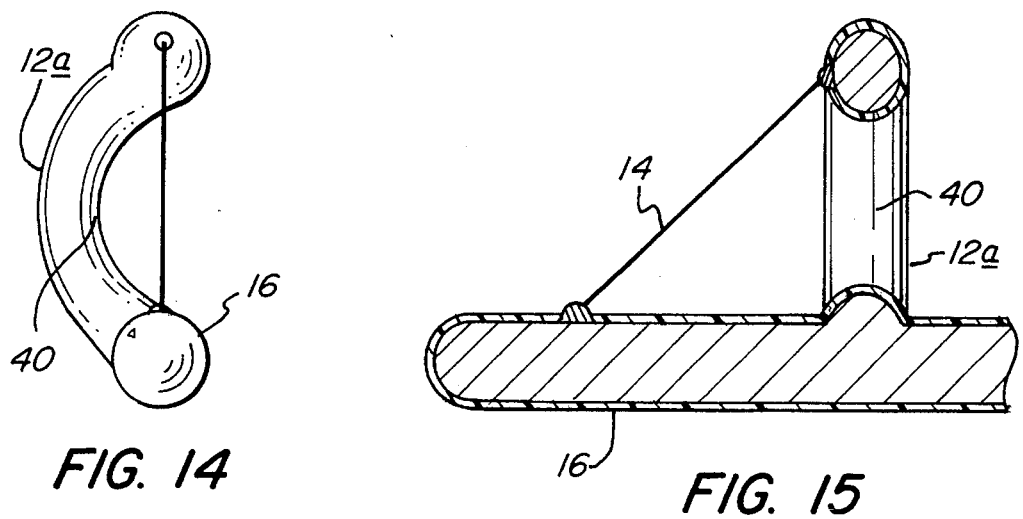
FIG. 14
FIG. 15

INSTRUMENT FOR ELECTRO-SURGICAL EXCISOR FOR THE TRANSFORMATION ZONE OF THE UTERINE CERVIX AND METHOD OF USING SAME

CROSS REFERENCE TO RELATED APPLICATION

The present application is a continuation-in-part application of my application Ser. No. 08/192,132 filed Feb. 4, 1994 now U.S. Pat. No. 5,403,310.

BACKGROUND OF THE INVENTION

The present invention relates to an electro-surgical excisor, and more particularly, to an electro-surgical excisor used for excising a tissue specimen from the transformation zone of the uterine cervix.

Cervical intraepithelial neoplasia has been on the increase in recent years, but successful ablation treatment has been provided by procedures such as electrocoagulation, electrodiathermy, cryosurgery, and laser surgery. With such procedures, it is important for the physician to recognize and biopsy invasive cancers to avoid their unintentional ablation.

Recently, biopsy specimens of this type of lesion has been successfully obtained by use of wire loop electrodes. Such electrodes allow the lesions and the transformation zone to be removed in their entirety and made available for a pathological analysis.

In using a loop electrode on the end of a handle, there is typically no guiding support during the excision. As a result, there is a risk of injury to the surrounding tissue which would result in a longer recovery period for the patient. Further, the amount of tissue obtained may vary in amount and definition, leading to difficulties in the pathological analysis.

It is an object of the present invention to provide a novel electro-surgical excisor which permits the complete severance of a controlled tissue specimen in a single revolution of the excisor.

It is also an object to provide such an electro-surgical excisor which minimizes the potential for injury to adjacent healthy tissue.

It is a further object to provide such an electro-surgical excisor which obtains a more defined and controlled amount of cervical tissue, making excision of the lesion and pathological interpretation easier.

SUMMARY OF THE INVENTION

It has now been found that the foregoing and related objects may be readily attained in an electro-surgical instrument for excision of a tissue specimen from the transformation zone of the uterine cervix, and it includes an elongated body member having an endocervical portion at one end, a contact portion at the other end, and a vaginal portion therebetween. The endocervical portion is insertable into and rotatable in the uterine cervix. A stop arm extends substantially at a right angle to the body member at the juncture of the endocervical portion and the vaginal portion, and a wire electrode extends diagonally from the stop arm to the endocervical portion. The elongated body member is dimensioned to extend outwardly of the vaginal canal when the endocervical portion is inserted into the uterine cervix to allow the instrument to be manipulated externally of the vaginal canal.

Generally, the endocervical portion is about 12–22 mm in length, and a unidirectional stop arm is about 10–20 mm in length, and each bidirectional stop arm is about 7.5–15 mm. The stop arm may extend in only one direction or in both directions from the body member.

The electrode is fastened to the endocervical portion at a point spaced inwardly from its free end, usually about 1–5 mm, and to the stop arm at a point spaced inwardly from its free end, generally about 1–3 mm for a bidirectional stop arm and 2–5 mm for a unidirectional stop arm.

In a preferred embodiment, the stop arm to which the electrode is attached has a laterally offset portion intermediate its length to enable viewing of the cervical area which is being cut by the electrode. The offset portion of the stop arm may be arcuate or generally V- or U-shaped.

In excising a specimen from the transformation zone of the uterine cervix, the endocervical portion of the instrument is inserted through the vaginal canal and into the endocervical canal of the uterine cervix until the electrode contacts an area of the ectocervix without colposcopically evident pathology. Because of the offset in the preferred stop arm, the physician can observe the placement and cutting action of the electrode over substantially its entire length. Current is supplied to the electrode and the instrument is advanced into the endocervical canal until the stop arm abuts the ectocervix. This cuts into the transformation zone of the uterine cervix, after which the instrument is rotated one full revolution about its axis with the stop arm abutting the ectocervix to cut a conically shaped tissue specimen from the transformation zone of the uterine cervix. The current to the electrode is discontinued, and the instrument and the specimen are withdrawn from the vaginal canal.

If so desired, only a partial revolution may be utilized to cut a wedge-shaped section with the instrument being withdrawn slowly at the end of the desired arc to cut the opposite end of the section.

Preferably, the current is of a value to effect both cutting and coagulation, generally to produce power in the range of 50–70 watts. The body portion of the electrode is dimensioned so that the insertion results in the body member extending outwardly of the vaginal canal with the endocervical portion in the uterine cervix; in this manner, the instrument is manipulated externally of the vaginal canal.

Usually, the current to the electrode is discontinued after the advancing step and before the rotating step to allow for preparation for the rotation step. Thereafter, the current is again supplied to the electrode prior to the rotating step.

BRIEF DESCRIPTION OF THE DRAWINGS

FIG. 1 is a perspective view of an electro-surgical excisor embodying the present invention;

FIG. 2 is a fragmentary plan view of the electrode end portion thereof showing the stop arm, electrode, and endocervical portion, drawn to a scale enlarged from that of FIG. 1;

FIG. 3 is a sectional view along the line 3—3 of FIG. 2 drawn to a still enlarged scale;

FIG. 4 is a fragmentary side view of the contact end portion of the electro-surgical excisor;

FIG. 5 is a diagrammatic view of the electro-surgical excisor being inserted into the vaginal canal and uterine cervix, and showing the excisor mounted in the manipulator of an electro-surgical unit;

FIG. 6 is a diagrammatic side view of the fragment only illustrated electro-surgical excisor seated in the endocervical canal with arrows showing rotation of the excisor for tissue excision;

FIG. 7 is a diagrammatic view similar to FIG. 6 after the excisor and excised tissue specimen have been withdrawn;

FIG. 8 is a perspective view of the tissue specimen after removal from the electro-surgical excisor;

FIG. 9 is a perspective view of an alternate embodiment of the invention in which the stop arm extends in both directions from the body;

FIG. 10 is a fragmentary sectional view of the embodiment of FIG. 9 drawn to an enlarged scale;

FIG. 11 is a view similar to FIG. 6 showing the manner in which the elements of the bidirectional stop arm seat about the cervix to increase stability;

FIG. 12 is a perspective view of a preferred embodiment of the excisor of the present invention;

FIG. 13 is a fragmentary side elevational view of the end portion of the excisor of FIG. 12;

FIG. 14 is a bottom end view thereof; and

FIG. 15 is a fragmentary sectional view of the excisor along the line 15—15 of FIG. 13.

DETAILED DESCRIPTION OF THE PREFERRED EMBODIMENT

Turning first to FIGS. 1–4, an electro-surgical excisor embodying the present invention is illustrated therein as having an elongated body member generally designated by the numeral 10, a stop arm 12, and an electrode 14. The body member 10 has an endocervical portion 16 at one end thereof, a contact portion 18 at its other end, and a vaginal portion 20 therebetween.

The stop arm 12 extends at a right angle to the body member 10, intersecting it at the juncture of the endocervical portion 16 and the vaginal portion 20. The electrode 14 is formed from a thin wire and extends diagonally from the stop arm 12 to the endocervical portion 16.

As best seen in FIG. 3, the body member 10 and stop arm 12 have an integrally formed core 22 formed of an electro-conductive material such as stainless steel. This core 22 is covered with a coating 24 of electrically insulating material such as polytetrafluoroethylene, or other insulating synthetic resin, except over the contact portion 18.

The stop arm 12 has an anchor bead 26 of electrically conductive material which is in electrical contact with the core 22 and spaced inwardly from the free end of the stop arm 12. 22 and spaced inwardly from the free end of the stop arm 12. Similarly, spaced inwardly from the free end of the endocervical portion 16 is a bead 28 which is in electrical contact with the core 22. The electrode 14 is bonded to the beads 26, 28, and thereby makes electrical contact with the core 22.

Referring to FIG. 4, the uncoated contact portion 18 is dimensioned to fit a manipulator 30, as shown in FIG. 5, of a standard electro-surgical unit (not shown) so that current will flow therethrough to the electrode 14.

As best seen in FIG. 5, the body member 10 of the electro-surgical excisor is dimensioned so that the contact portion 18 is disposed outwardly of the vaginal canal 32 when the endocervical portion 16 is inserted into the endocervical canal 34 of the uterine cervix 36.

In a working embodiment, the elongated body member 10 is about 120–140, and preferably 130, mm in length, with an endocervical portion 16 of about 18–22, and preferably 20, mm, a vaginal portion 20 of about 80–100, and preferably 90, mm, and a contact portion 18 of about 8–12, and preferably 20, mm. The stop arm 12 is about 10–20, and preferably 15 mm in length. The anchor bead 26 is positioned on the stop arm 12 about 2–5, and preferably 4, mm from its free end, and the anchor bead 28 is positioned on the endocervical portion 16 approximately 2–5 mm from its free end.

The use of the electro-surgical excisor is shown in FIGS. 5–8. Referring first to FIG. 5, the endocervical portion 16 of the excisor is inserted through the vaginal canal 32 and into the endocervical canal 34 of the uterine cervix 36 until the electrode 14 contacts an area of the ectocervix 38 which is free from colposcopically evident pathology. Through use of the manipulator 30, current is imparted to the electrode 14, and the endocervical portion 16 is advanced in the direction shown by the arrow in FIG. 5 into the endocervical canal 34 until the stop arm 12 abuts the ectocervix 38 as shown in FIG. 6. In this manner, a cut is made in the transformation zone 40 of the uterine cervix 36 by the electrode 14. Because the stop arm 12 is seated stably on the ectocervix 38 and the electrode 14 is taut, the physican has good control of the cutting action, and the extent of penetration is limited.

At this point, current to the electrode 14 may be discontinued to permit preparation for the next step. Once preparation is completed, current is again imparted to the electrode 14 and the excisor is rotated one full revolution along its axis, as shown by the arrows in FIG. 6. Because rotation takes place with the endocervical portion 16 in the endocervical canal 34, and with the stop arm 12 abutting the ectocervix 38, the excisor is stabilized, allowing for a conically shaped tissue specimen 42 to be excised from the transformation zone 40 of the uterine cervix 36.

Once the excision is complete, current is discontinued to the electrode 14 and the excisor is withdrawn from the endocervical canal 34 and the vaginal canal 32, withdrawing the tissue specimen 42 with it. As shown in FIG. 8, the tissue specimen 42 will be conical in shape providing a defined and controlled amount of cervical tissue to make pathological interpretation easier and more reliable. The current employed for the excision process is one appropriate for cutting and coagulation and will typically provide an output power in the range of 50–70 watts. If so desired, only a wedge-shaped specimen may be cut by limiting the extent of rotation and then slowly withdrawing the instrument to cut the end of the section.

In FIGS. 9 and 10, there is shown an alternate embodiment of the invention in which the stop arm 12 extends in both directions from the body member 10. This increases the surface of the cervix against which the instrument will bear while allowing a reduction in the length of the arm if it were to project in only one direction. In this embodiment, each projecting length will normally be 7.5–10 mm and the electrode may be spaced closer to the free end, i.e., about 1–2 mm. FIG. 11 illustrates the manner in which the bidirectional stop arm seats on opposite sides of the cervical canal to increase stability during rotation.

Turning next to the embodiment of FIGS. 12–15, this excisor has a stop arm 12a which has a laterally offset portion 40 of arcuate configuration so that most of the stop arm 12 is offset from the longitudinal plane extending through the electrode 14 and body member 10. As a result, the physician can see most of the cervical area which is being cut by the electrode and which would otherwise be obscured by the stop arm 12a. However, the stop arm 12a seats about the ectocervix 38, and the excisor is stabilized and limited as to the amount of penetration.

Electro-surgical excisors having the electrode positioned at varying angles, as appropriate for different clinical situations, may be fabricated by altering the position of anchor bead 26 on stop arm 12 and/or the position of anchor bead 28 on endocervical portion 16.

Thus, it can be seen from the foregoing detailed specification and attached drawings that the novel electro-surgical excisor of the present invention enables complete severance of the cervical tissue in a single revolution of the excisor while preventing injury to the adjacent healthy tissue. Additionally, use of the excisor enables the excisor of a defined and controlled amount of cervical tissue, making excision of the lesion and pathological interpretation easier. No special equipment is necessary for the excisor of the present invention which may be utilized in existing electro-surgical apparatus.

Having thus described the invention, what is claimed is:

1. An electro-surgical instrument for excision of a tissue specimen from a transformation zone of a uterine cervix by insertion through a vaginal canal comprising:
    (a) an elongated body member having two ends with an endocervical portion adjacent one end, a contact portion adjacent a second end, and a vaginal portion therebetween, said endocervical portion being insertable into and rotatable in uterine cervix;
    (b) a stop arm extending substantially at a right angle to said body member at a juncture of said endocervical portion and said vaginal portion, said stop arm having a laterally offset portion intermediate its length; and
    (c) a wire electrode extending diagonally from adjacent an outer end of said stop arm to said endocervical portion, said offset portion of said stop arm enabling visual observation of a cervical area to be cut by the wire electrode.

2. The electro-surgical instrument in accordance with claim 1 wherein laterally offset portion of said stop arm is of arcuate configuration.

3. The electro-surgical instrument in accordance with claim 2 wherein the outer end of said stop arm is the outer end of said offset portion of arcuate configuration.

4. The electro-surgical instrument in accordance with claim 1 wherein said elongated body member is dimensioned to extend outwardly of the vaginal canal when the endocervical portion is inserted into the associated uterine cervix to allow said instrument to be manipulated externally of the vaginal canal.

5. The electro-surgical instrument in accordance with claim 1 wherein said electrode is fastened to said endocervical portion at a point spaced inwardly from said one end of said body member.

6. A method for excising a specimen from a transformation zone of a uterine cervix of a patient by insertion through a vaginal canal comprising the steps of:
    (a) providing an electro-surgical instrument comprising an elongated body member having two ends with an endocervical portion adjacent one end, a contact portion adjacent a second end, and a vaginal portion therebetween, a stop arm extending substantially at a right angle to said body member at a juncture of said endocervical portion and said vaginal portion, said stop arm having a laterally offset portion intermediate its length and a wire electrode extending diagonally from adjacent an outer end of said stop arm to said endocervical portion;
    (b) inserting said endocervical portion of said instrument through the vaginal canal and into the endocervical canal of the uterine cervix of a patient until said electrode contacts an area of ectocervix without colposcopically evident pathology;
    (c) imparting current to said electrode;
    (d) advancing said instrument into said endocervical canal until said stop arm abuts said ectocervix, said laterally offset portion of said stop arm enabling visual observation of cervical area being cut by the electrode, thereby cutting into the transformation zone of said uterine cervix with said electrode;
    (e) rotating said instrument about its axis with said stop arm abutting said ectocervix to cut a tissue specimen from said transformation zone of said uterine cervix;
    (f) discontinuing current to said electrode; and
    (g) withdrawing said instrument and said specimen from the vaginal canal.

7. The method for excising a specimen in accordance with claim 6 wherein the current imparting step involves imparting a current of a value to effect both cutting and coagulation.

8. The method for excising a specimen in accordance with claim 6 wherein said current produces power in a range of 50–70 watts.

* * * * *